US012758266B2

(12) United States Patent
Schultz

(10) Patent No.: US 12,758,266 B2
(45) **Date of Patent: *Oct. 13, 2026**

(54) TENSEGRITY EXTERNAL FIXATION SYSTEM TO DISTRACT BONES

(71) Applicant: Brent Schultz, Scottsdale, AZ (US)

(72) Inventor: Brent Schultz, Scottsdale, AZ (US)

( * ) Notice: Subject to any disclaimer, the term of this patent is extended or adjusted under 35 U.S.C. 154(b) by 356 days.

This patent is subject to a terminal disclaimer.

(21) Appl. No.: 18/392,233

(22) Filed: Dec. 21, 2023

(65) Prior Publication Data

US 2024/0122625 A1 Apr. 18, 2024

Related U.S. Application Data

(63) Continuation of application No. 17/916,603, filed as application No. PCT/US2022/011196 on Jan. 4, 2022, now Pat. No. 11,849,974.

(Continued)

(51) Int. Cl.
*A61B 17/66* (2006.01)
*A61B 17/64* (2006.01)
*A61B 17/60* (2006.01)

(52) U.S. Cl.
CPC .......... *A61B 17/66* (2013.01); *A61B 17/6425* (2013.01); *A61B 2017/606* (2013.01)

(58) Field of Classification Search
CPC . A61B 17/66; A61B 17/6491; A61B 17/6425; A61B 2017/606; A61B 2017/564–567
See application file for complete search history.

(56) References Cited

U.S. PATENT DOCUMENTS 5,074,865 A * 12/1991 Fahmy ............... A61B 17/6425 606/57
5,885,290 A 3/1999 Guerrero et al.

(Continued)

FOREIGN PATENT DOCUMENTS

DE 3807335 A 9/1989
FR 2855040 A 11/2004

(Continued)

OTHER PUBLICATIONS

USPTO, International Search Report and Written Opinion On Patentability, PCT/SU22/11196, May 6, 2022.

*Primary Examiner* — Eduardo C Robert
*Assistant Examiner* — Michelle C Green
(74) *Attorney, Agent, or Firm* — Invention To Patent Services; Alex Hobson

(57) ABSTRACT

A tensegrity external fixation system utilizes a tensegrity external fixator having a compression portion and a tension portion that create a force to distract bone. A tensegrity external fixator has a compressor assembly with an extension that is compresses by a tension element, such as a tension band. In an embodiment, the tension band is coupled with a bone via a stud that is attached to the bone. The tension band may extend through a stud retainer, such as a loop coupled with the stud. A single extension may be used and compressed to cause the extension to bow between a tension band or wires. In an exemplary embodiment, a compressor assembly has a compression element that is compressed by the one or more extensions. Two extensions may extend from a compressor coupling having a compression element and manipulation of the extensions may place the compression element in compression.

20 Claims, 16 Drawing Sheets

Related U.S. Application Data

(60) Provisional application No. 63/133,448, filed on Jan. 4, 2021.

(56) References Cited

U.S. PATENT DOCUMENTS

| | | | | |
|---|---|---|---|---|
| 2005/0203509 | A1* | 9/2005 | Chinnaian | A61B 17/6491 606/54 |
| 2006/0058796 | A1* | 3/2006 | Hartdegen | A61B 17/7059 606/291 |
| 2011/0034924 | A1 | 2/2011 | Tan | |
| 2011/0218535 | A1* | 9/2011 | Wang | A61B 17/8071 606/71 |
| 2012/0226277 | A1* | 9/2012 | Tan | A61B 17/6483 606/59 |
| 2014/0336648 | A1* | 11/2014 | Van Aaken | A61B 17/6441 606/58 |
| 2018/0116810 | A1 | 5/2018 | Rifkin | |
| 2019/0091060 | A1 | 3/2019 | Shah | |
| 2020/0375628 | A1* | 12/2020 | Foo | A61B 17/6425 |

FOREIGN PATENT DOCUMENTS

| | | | | |
|---|---|---|---|---|
| FR | 2855040 | A1 * | 11/2004 | A61B 17/66 |
| GB | 2573000 | A | 10/2019 | |

* cited by examiner

TENSEGRITY EXTERNAL FIXATION SYSTEM TO DISTRACT BONES

CROSS REFERENCE TO RELATED APPLICATIONS

This application is a continuation of U.S. patent application Ser. No. 17/916,603, filed on Oct. 3, 2022 and currently pending, which is a national stage application of international application No. PCT/US2022/011196, filed on Jan. 4, 2022, which claims the benefit of priority to provisional patent application No. 63/133,448, filed on Jan. 4, 2021; the entirety of each prior application is hereby incorporated by reference herein.

BACKGROUND OF THE INVENTION

Field of the Invention

The invention relates to an external fixation system that utilizes a tensegrity structure formed by tension bands that extend between studs coupled to the bone and a compressor assembly.

Background

Dynamic external fixation is used to stabilize fractures across joint surfaces, such as finger, toe, and elbow joints, yet still allow those joints to move. The simplest dynamic fixators utilize hinges that are typically located at the point of isometry of the joint. These devices hold joints apart via traction provided by a hinged bar and the bar holds the fractured bones in stabilizing tension by sustaining a compression moment. These devices require a rigid connection between the bone and the tension generating elements, usually via pins.

Currently available external fixators for fingers are only configured for application to the lateral portion or side of the finger, making them obtrusive and uncomfortable for the patient.

SUMMARY OF THE INVENTION

The invention is directed to a tensegrity external fixation system that utilizes a tensegrity external fixator having a compression assembly with a compression portion and a tension portion that together create a force to distract bone. An exemplary tensegrity external fixator has a compressor assembly with an extension that is compresses by a tension element, such as a tension band. In an exemplary embodiment, the tension band is coupled with a bone via a stud that is attached to the bone. The tension band may extend through a stud retainer, such as a loop or detent coupled with the stud or formed in the stud. A single extension may be used and compressed to cause the extension to bow between a tension band or bands. In an exemplary embodiment, a compressor assembly has a compression element that is compressed by the one or more extensions. Two or more extensions may extend from a compressor coupling having a compression element and manipulation of the extensions may place the compression element in compression. The tension band coupled to the one or more extensions may retain the extensions in a compressed configuration, which maintains the tension band in tension. The forces are balanced with the tension band exerting a distraction force on a stud.

In an exemplary embodiment, a tensegrity external fixation system is used to distract bone across a fracture, wherein a first stud is coupled to a bone on one side of the fracture and a second stud is coupled to a bone on the opposing side of the fracture. The two studs place the fracture and bone in tension to allow for proper healing and bone alignment. This type of system may be well suited for compression factures and especially for compression factures of smaller bones, such as those in the hand and foot. A stud has an insert end that is inserted into a body part, such as a bone and an exposed end that extends out from the body part, such as the bone. The exposed end may extend out of the body or out from the skin of the patient and the compressor and the stud retainer may be external the body. An exemplary tensegrity external fixator may be configured as an implantable device and the exposed end may be internal the body but outside of a body part configured for distraction or traction.

An exemplary tensegrity external fixation system may enable a bone fractured proximal to a joint to be distracted across the joint and enable movement of the joint to provide a desired result, properly aligned bones across the fracture and full range of motion of the joint. In many cases, fractured bones across a joint are stabilized but this leads to loss of range of motion. In addition, the tensegrity external fixator may be coupled to a finger on dorsal side, or top side, lateral side or side of the finger or even the ventral side, or underside of the finger, or any non-standard plane. An exemplary tensegrity external fixator may be configured to flex or move with the movement of the bones across the joint. In addition, the amount of distraction tension may be adjusted as the bones heal to provide proper bone alignment across the joint.

An exemplary tensegrity external fixation system may employ a single extension that extends distal the studs on either side of a fracture. The single extension may be compressed and bow under the compression, wherein a tension band pulls on the studs to keep the extension in compression. An extension may have a tension retainer on the extended ends of the extension and the tension retainer may be configured to couple with a tension band. A tension retainer may be a loop, hook or a notch for example. A single tension band may be coupled with tension retainers and extend to a stud retainer to pull the stud away from the fractured portion of the bone. A separate tension band may be configured on each side of the fracture and the compressor assembly, or by be coupled with the tension retainer on the opposing ends of the extension or extensions.

A single stud may be placed on opposing sides of the bone from the fracture or two studs may be secured to the bone on both sides of the fracture. When two studs are configured on a side of the fracture bone, a single tension band may secure the extension in compression on that side of the fracture. Any number of arrangements of studs, extensions and wires may be employed to place the extension(s) in compression and the tension band in tension. Therefore, in an exemplary embodiment, two separate tension bands are used, a first tension band that is coupled between a first extended end and tension retainer of at least one extension and the stud or studs on a first side of a bone fracture, and a second tension band that is coupled between a second extended end and tension retainer of at least one extension and the stud or studs on a second side of a bone fracture.

In an exemplary embodiment, a compressor assembly comprises a first pair of extensions that extend to a first side of the bone fracture and a second pair of extensions that extend to a second side of the bone fracture. These pair of extensions may extend out at an angle away from each other and the bone and moving the extended ends of the pair of extension towards each other compresses the compressor coupling or compression element, which may employ a spring. The extensions may be metal arms that act like a spring when deflected from an attachment with the compressor coupling. A compressor may comprise wrapped or twisted or tied portions of a first extension with a second extension.

A compressor coupling may comprise an attachment for the coupled end of the extension or extensions. The extensions may be defected within an elastic region of the material and thereby create and maintain a tension on the tension band coupled thereto. For example, a metal arm, such as a rod of metal may be bent or deflected within an elastic region, wherein it will spring back to an original position upon removal of the deflecting load. A compressor coupling may comprise a coupling of two or more extensions, such as the extensions being wrapped or tied around each other.

An exemplary compressor coupling may comprise a compression element, such as a spring or an elastic element that exerts a force on the extension or extensions when compressed. A single compression element may be used for one or more of the extensions. In an exemplary embodiment, each pair of extensions has a compression element configured between them, whereby when the pair of extensions are deflected toward each other, the compression element is compressed.

An exemplary extension is an elongated member, having a length that is at least three times greater than a width, or diameter. An exemplary extension is a rod of metal such as stainless steel or spring steel and may be a shape memory metal such as an alloy of nickel and titanium, nitinol. A nitinol alloy may have a shape memory that causes the extension to produce a force to return to the pre-deflected shape or position.

A tensioning device may be coupled with the tension band to apply tension to the wire. A tensioning device may comprise a tensioning controller and a tension sensor, such as a strain gauge. A surgeon may dial in the amount of tension desired and the tensioning device may maintain this tension in the tension band even as the studs move apart. As the studs move apart, the tension band or wires will relax as the tension in the wire is reduce due to the tensegrity assembly.

A tension band may be metal wire including, but not limited to, steel, aluminum, titanium, and nitinol and may extend on one side of the bone fracture or may extend across the bone fracture from the first stud to the second stud. A tension band may be an elastic band that maintains tension and may be more flexible than a metal wire. An elastic band type tension band may be used as the bone fracture heals to allow more mobility of the joint and more flexure of the bones about the joint. An elastic material is a material that can be extended and return substantially to an un-extended state (within about 10% of an original length), upon removal of an extension force.

An exemplary tensegrity external fixation system may incorporate a torque stabilizer to prevent the stud from being moving the bones into an undesirable orientation. The tension band pulling on the stud retainer will create a torque force or moment that may cause the bone to not just distract but rotate or move in response to the moment. A torque stabilizer may extend up from the stud retainer and a torque stabilizer coupler may be coupled to a torque stabilizer retainer to produce a counter torque force on the stud retainer to balance the moments. In this way, the stud retainer may be pulled away from the fractured bone and the moments may be effectively reduced to prevent undesirable bone displacement.

An exemplary tensegrity external fixation system may employ studs having one, two or more insert ends that extend into the bone to prevent deflection of the stud due to the forces and moments created by the compression assembly coupled to the stud retainers.

An exemplary tensegrity external fixation system may be used on any suitable bone fracture wherein a stud can be coupled with the bone on either side of the fracture. In particular, a tensegrity external fixation system may be configured on smaller bones, such as those in the foot or hands.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

Figure 1:
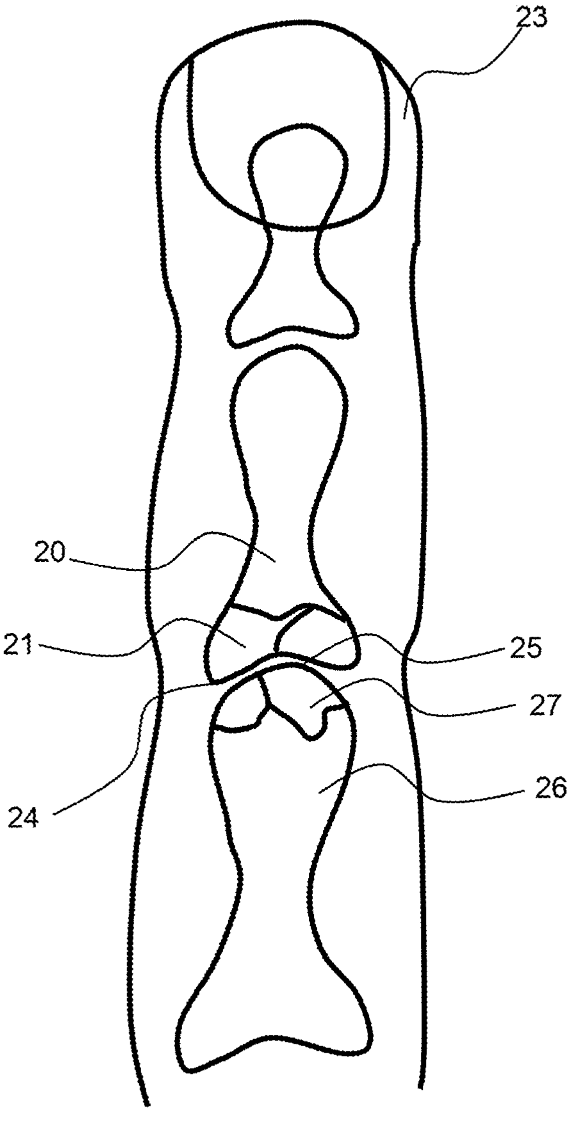
FIG. 1 shows a top view of a bone fracture of two bones of a finger, wherein the fracture is on either side of a joint.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms “comprises,” “comprising,” “includes,” “including,” “has,” “having” or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of “a” or “an” are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

As shown in FIG. 1, a bone is fracture at the joint. These fractures are difficult to treat as immobilizing the joint for bone healing can result in the loss of range of motion at the joint. In addition, some joint fractures are impacted fractures requiring the bones on either side of the joint to be distracted, or pulled apart during bone healing. As shown, the finger 23 has a first bone 20 that has a bone fracture 21 and a second bone 26 with a second bone fracture 27. The two bone fractures are on either side of the joint 24 or bone gap 25.

Figure 2:
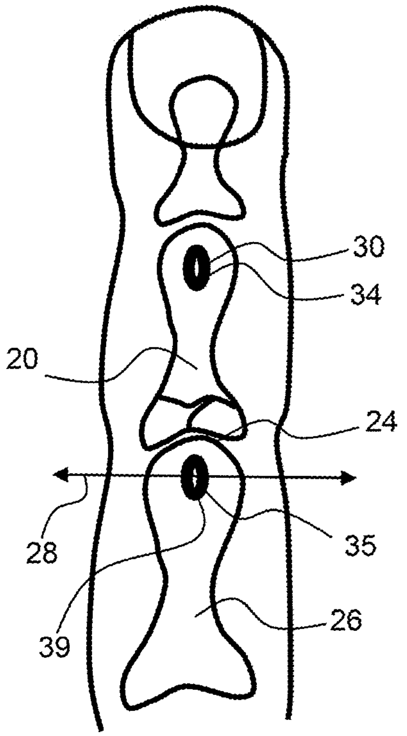
FIG. 2 shows a top view of a finger having a first stud in a first bone and a second stud in a second bone on either side of a joint or bone gap wherein there is a fracture.
Figure 3:
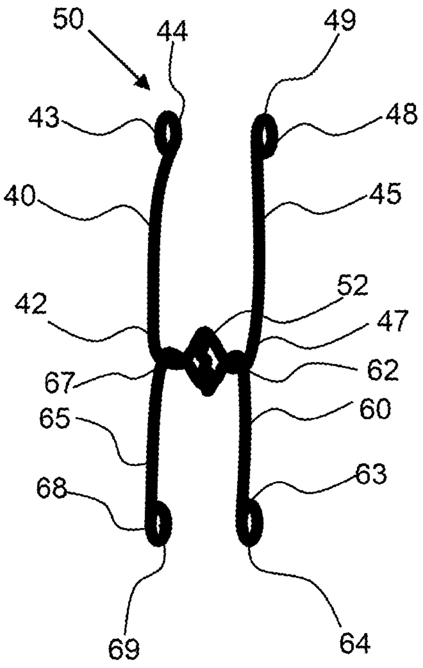
FIG. 3 shows a top view of an exemplary compressor assembly that includes a plurality of extensions coupled with a compressor coupling.
Figure 4:
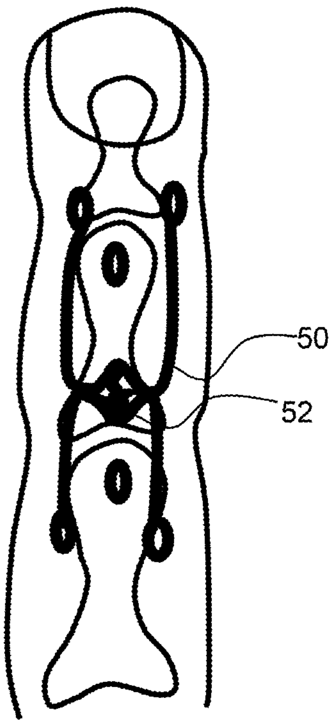
FIG. 4 shows a top view of the compressor assembly of FIG. 3 located over the fracture with the extended ends of the extensions extending distal the studs from the fractured bone.
Figure 5:
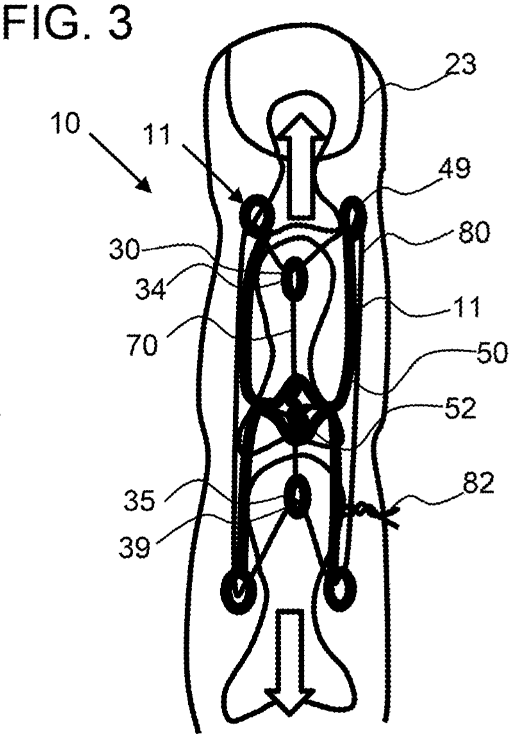
FIG. 5 shows a top view of a tensegrity external fixator system having a tension band coupled with the compressor assembly, wherein the tension band exerts a tension force on the bones to distract the first and second bones to allow proper bone healing of the fracture.

Referring now to FIGS. 2 to 5, an exemplary tensegrity external fixator system 10 utilizes studs 30, 35, coupled to the bone, and a compressor assembly 50 that is compressed to keep tension force on a tension band 80. The tension band 80 is coupled with the compressor assembly to keep the compressor in compression to balance the forces. As shown in FIG. 2, a finger 23 has a first stud 30 in a first bone 20 and a second stud 35 in a second bone 26, wherein the studs are located on either side of a joint 24 or bone gap wherein there is a fracture. As shown in FIG. 4, a compressor assembly 50, as shown in FIG. 3 is configured over the finger with the compressor coupling 52 over the joint. The exemplary compressor assembly 50 has four extensions 40, 45, 60, 65 with pairs of extensions extending to opposing sides of the compressor coupling 52. The compressor coupling couples the coupled extensions together such that the compressor coupling is compressed when the extensions are retained by the tension band, as shown in FIG. 5. The extension of the compressor coupling may have a tension retainer 44, 49, 64, 69 on each of the extensions 40, 45, 60, 65, respectively. These tension retainers may be partial loops or rings that are configured to retain the tension band thereto. The first stud 30 and the second stud 35 may have a stud retainer 34, 39, respectively, such as a partial loop or ring, or indentation, to enable the tension band to be retained to the stud. The tension band extends through the stud retainers and the tension retainers on the extensions to form the tensegrity external fixator 11. The extensions may have separate coupled ends 42, 47, 62, 67 or may be formed from two extensions wherein the two extensions are coupled together to form the compressor coupling 52. The tension band 80 may be a tension wire that has a tension band coupling 82, wherein the tension wire is twisted together to produce a desired tension force.

Figure 6:
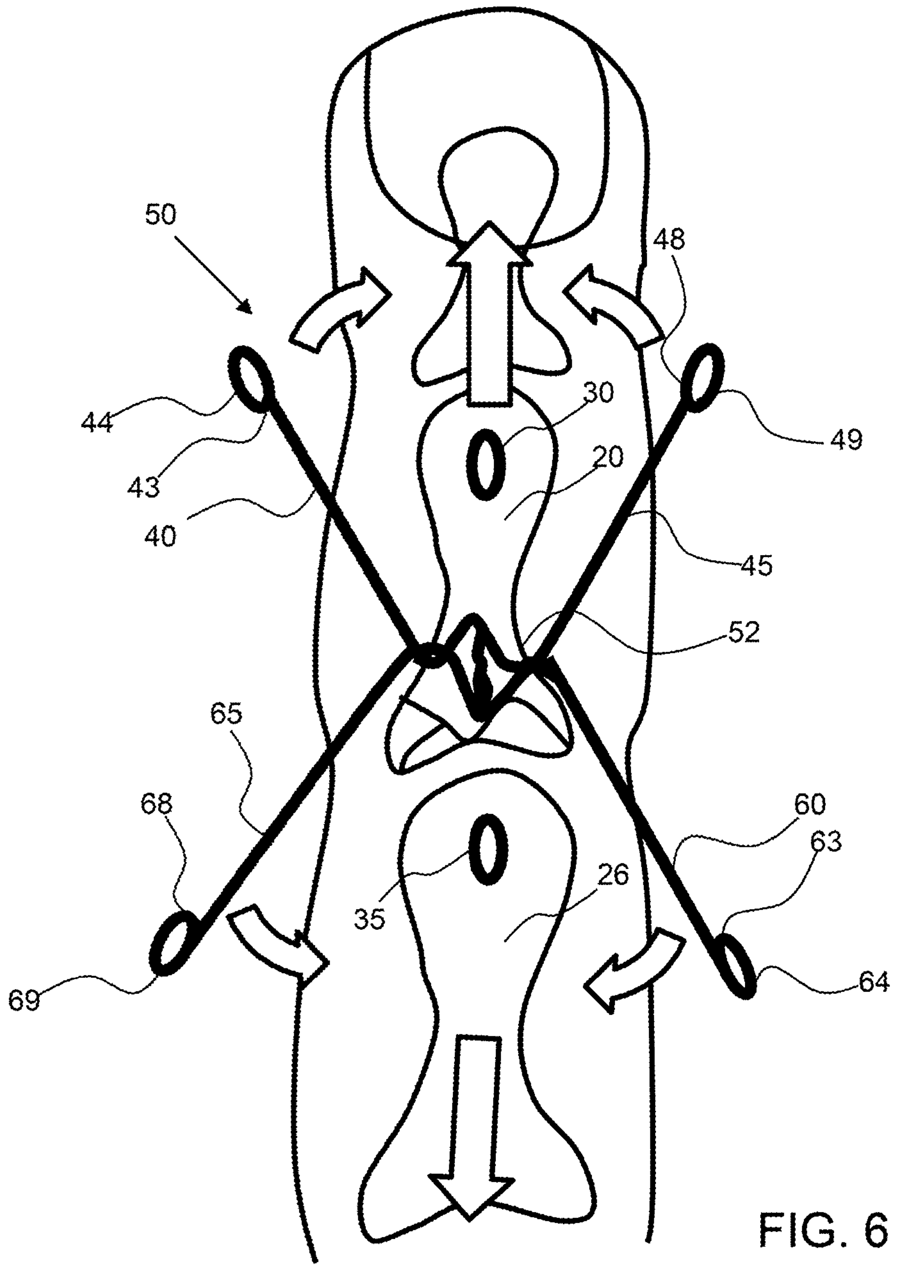
FIG. 6 shows a top view of an exemplary compressor assembly located over a fractured bone with the extended ends of the extensions extending distal the studs from the fractured bone.

As shown in FIG. 6, an exemplary compressor assembly 50 incorporates two contiguous extensions that are coupled together to form the compressor coupling 52. Each of the extended ends 43, 48, 63, 68 of the extensions has a tension retainer 44, 49, 64, 69, a hoop thereon. The bold arrows show that the extensions will be pulled toward each other, on opposing sides of the fracture and this puts the compressor coupling in compression. The tension band will hold the extensions in this compressed state and therefor the tension band will be held in tension.

Figure 7:
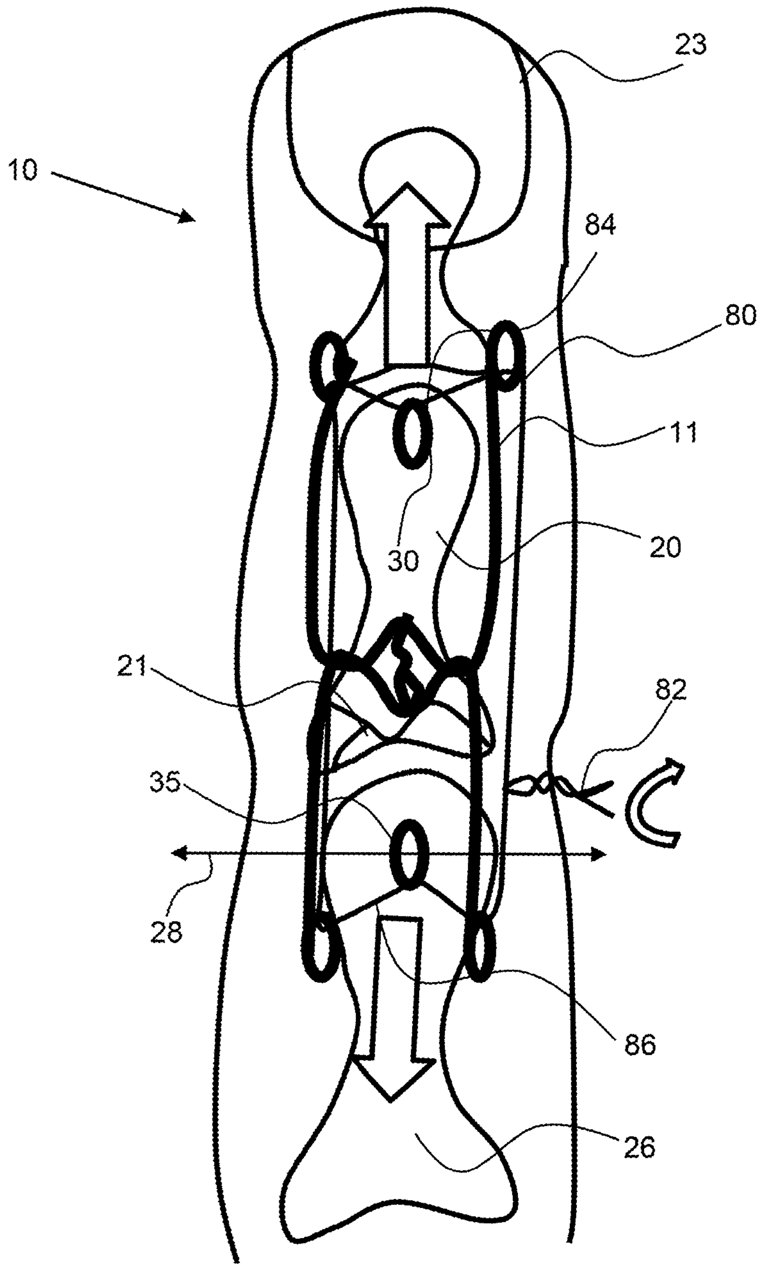
FIG. 7 shows a top view of an exemplary tensegrity external fixator system attached to a first and second bone to distract the bones and the fractured bone for proper healing.

As shown in FIG. 7, the tension band 80 is coupled with the compression assembly 50 by extending through the tension retainers of each of the extensions and also extending through the stud retainers of the two studs 30, 35. The tension band is held in tension by the compressor assembly and pulls the two studs apart, or away from each other, as indicated by the large arrows. This produces a first tension segment 84 on the first stud 30 and a second tension segment 86 on the second stud 35. The tension band may be coupled together in a tension band coupling 82. A coupling may have a tension element to produce a desired amount of tension on the tension band. This might change the angle of the extensions, for example. The tension band coupling may simply be the tension band twisted or otherwise tied together.

Figure 8:
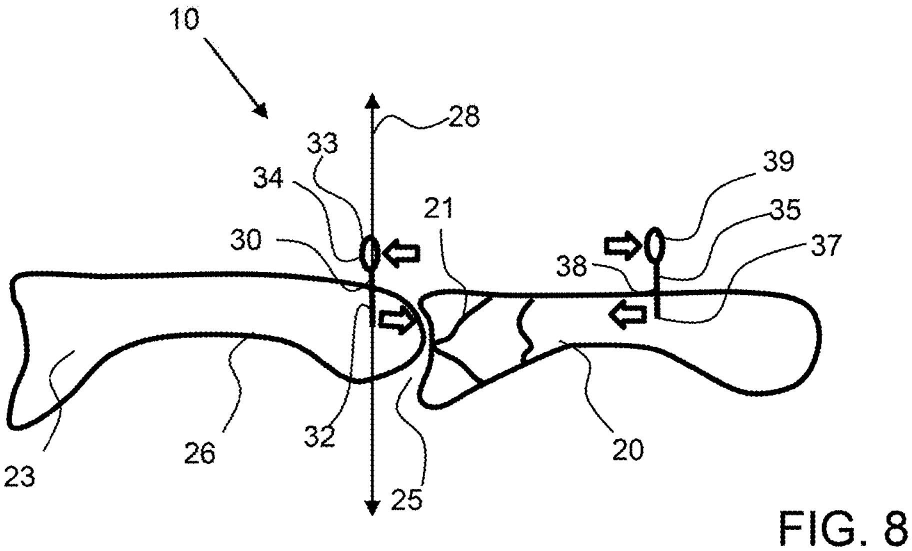
FIG. 8 shows a side view of a finger having a first stud in a first bone and a second stud in a second bone on either side of a joint or bone gap; wherein there is a fractured bone, and bold arrows indicating the forces exerted on the insert end and the exposed ends of the studs to produce a torque force. The exposed end are outside of the body of the patient, such as extending out from the patient's skin.
Figure 9:
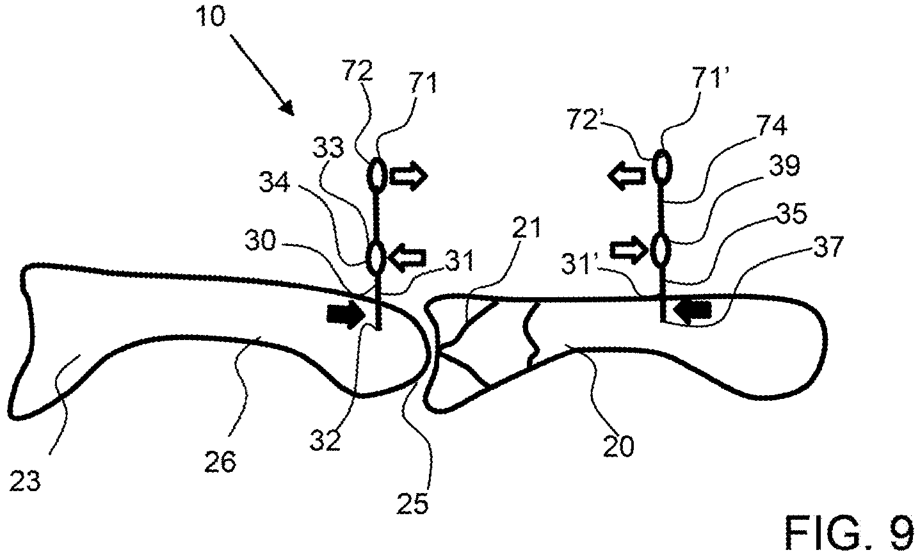
FIG. 9 shows a side view of a finger having a first stud in a first bone and a second stud in a second bone on either side of a joint and a torque stabilizer extending up from the stud retainers to balance the torque forces on the stud retainers.

As shown in FIGS. 8 and 9, an exemplary tensegrity external fixator system 10 utilizes studs 30, 35, coupled to the bone. A first stud 30 is coupled to a second bone 26 along the center of rotation 28 of the first bone 20. The first stud has an insert end 32 and an exposed end 33, that is exposed from the skin, and a stud retainer 34. The second stud 35 also has an insert end 37 and a stud retainer 39. When a tension band is coupled to the stud retainers, a distraction force, as indicated by the large bold arrows, forces the two studs, and the bone coupled thereto, apart. The bone provides an opposing force as indicated by the solid bold arrows on the bone. The force on the studs creates a torque on the stud posts 31, 31' which may torque the bone or bones out of alignment. It is desirable to maintain a distraction force on the bones without applying a torque or moment on the bones in anyway. As shown in FIG. 9, torque stabilizers 71, 71' are coupled with the studs 30, 35, respectively. A torque stabilizer coupler (not shown) may be configured across the torque stabilizer retainers 72, 72' to balance the torque on the stud. This balance of the torque or moment on the stud may enable the studs to distract the bones and maintain the bones in alignment.

Figure 10:
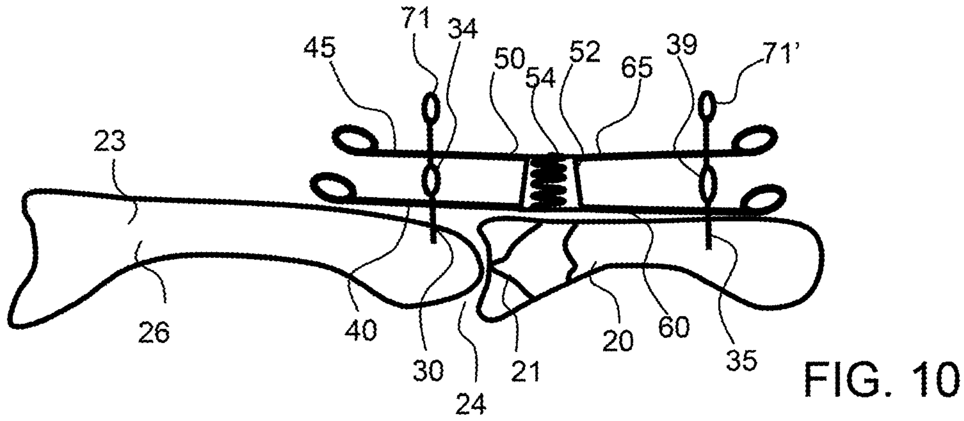
FIG. 10 shows a side view of an exemplary compressor assembly located over the fracture with the extended ends of the extensions extending distal the studs from the fractured bone.
Figure 11:
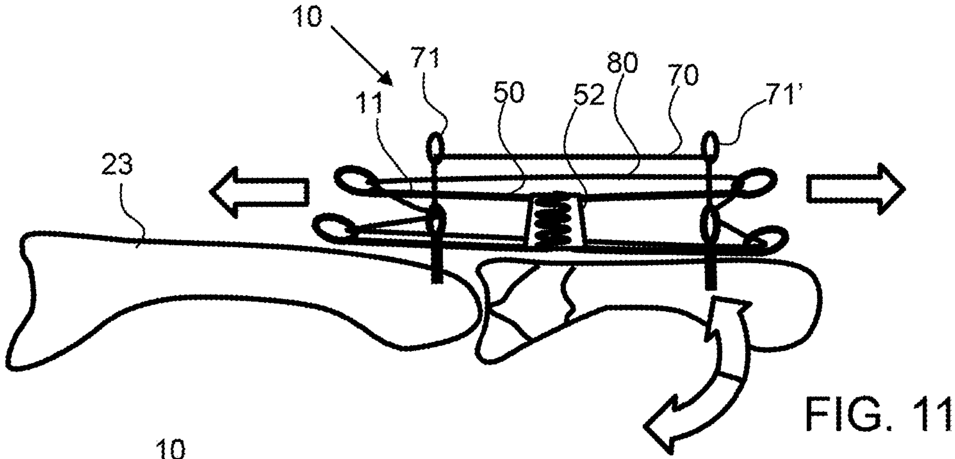
FIG. 11 shows a side view of a tensegrity external fixator having a tension band coupled with the compressor assembly to form a tensegrity external fixator, wherein the tension band exerts a tension force on the bones to distract the first and second bones to allow proper bone healing of the fracture.
Figure 12:
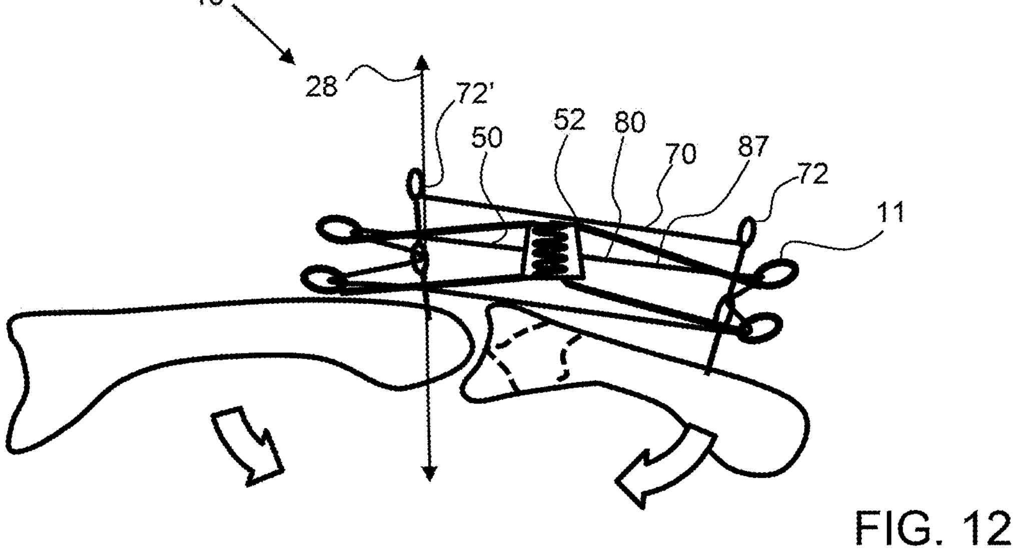
FIG. 12 shows a side view of the tensegrity external fixator system coupled across the joint of the fractured finger, wherein the finger can freely bend across the joint.

Referring now to FIGS. 10 to 12, an exemplary tensegrity external fixator system 10 utilizes studs 30, 35, coupled to the bone, and a compressor assembly 50 that is compressed to keep tension force on a tension band 80. The extensions on either side of the compressor assembly are forced together thereby creating and maintaining a tension force on the tension band 80. The tension band is coupled with the compressor assembly to keep the compressor in compression to balance the forces. As shown in FIG. 10, a finger 23 has a first stud 30 in a second bone 26 and a second stud 35 in a first bone 20, wherein the studs are located on either side of a joint 24 or bone gap wherein there is a bone fracture 21. The studs have stud retainers 34, 39, such as a hoop or detent in the stud to retain the tension band to the stud. The compressor assembly 50, is configured over the dorsal side, or top of the finger 23 with the compressor coupling 52 hovering over the finger to allow movement of the finger about the join. The exemplary compressor assembly 50 has four extensions 40, 45, 60, 65, with pairs of extensions extending from opposing sides of the compressor coupling 52. The compressor coupling has a compression element 54 that produces a force on the extensions outward. The compression element may be spring or simply an attachment of the extension, wherein the extension produces a force when deflected about the attachment to the compressor coupling.

As shown in FIG. 11, the tension band 80 couples the compressor assembly 50 and the studs to create a tension force on the two studs to distract the two bones and the fracture. The finger 23 can flex about the joint 24, as the tensegrity external fixator 11 is flexible and offset from the finger.

As shown in FIG. 12, the tensegrity external fixator 11 is coupled across the joint of the fractured finger, wherein the extensions are curved or bent extending from the compressor coupling 52 and wherein the finger can more freely bend across the joint. Also, in this embodiment, the tension band 80 is an elastic band. As described herein, a tension band may be an elastic band as the fracture heals, as indicated the dashed factures in the bones. This tension band may be changed to an elastic band when the facture is healed to an effective amount.

Figure 13:
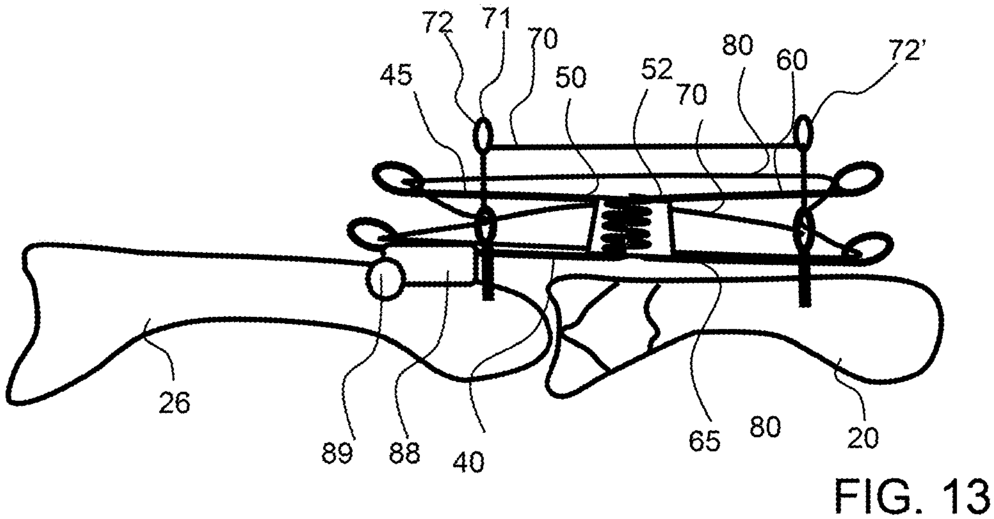
FIG. 13 shows a side view of the tensegrity external fixator coupled across the joint of the fractured finger having a tensioning device coupled with the tension band.

As shown in FIG. 13, the tension band is coupled with a tensioning device 88 that maintains tension on the tension band 80. A tensioning device may have in inlet and outlet for the tension band and may precisely control the Newtons of tension in the tension band. A tensioning device may be programmed to gently ease tension forces as bones heal (adding flexibility to the construct) or maintain constant tension or rhythmically apply tension which is commonly used in osteogenic distraction. This may stimulate biologic differentiation of bone or related tissues such as cartilage. A tensioning device may have a tension control feature 89 to enable a desired amount of tension to be set, such as a knob or dial. A tensioning device may include a strain gauge that measures the amount of tensile force in the tension band and a desired tensile force may be set and maintained by the tensioning device.

Figure 14:
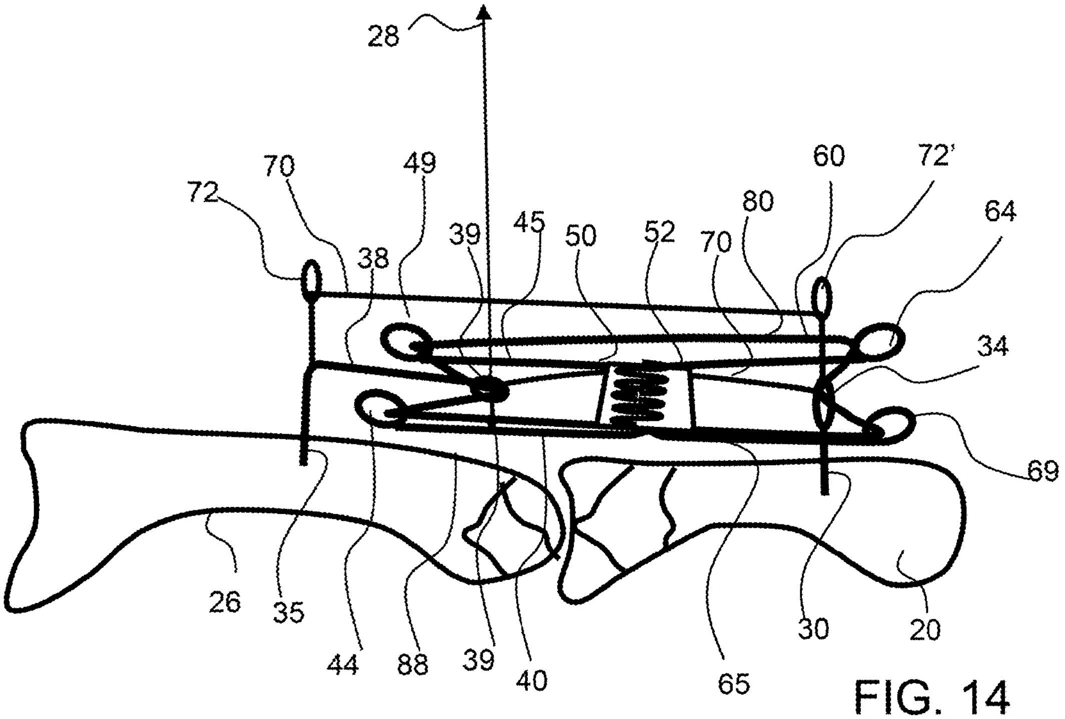
FIG. 14 shows a side view of the tensegrity external fixator coupled across the joint of the fractured finger having a stud extension extending from the second stud to located the stud retainer over the center of rotation.

As shown in FIG. 14, the exemplary tensegrity external fixator 11 is coupled across the joint of the fractured finger and has a stud extension 38 extending from the second stud 35 to located the stud retainer 39 over the center of rotation 23 of the first bone 20 about the second bone 26, or about the joint.

As shown throughout FIGS. 11 to 14, a torque stabilizer 71 may be coupled to each of the first stud 30 and second stud 35 to promote proper alignment of the bones during healing. The torque stabilizer coupler 70, such as an elastic band or spring wire extends from the torque stabilizer retainers 72, 72'. The tension band will distract the stud at the stud retainer and this will create a torque force on the bone. The torque stabilizer 71 may be used to counter this torque by applying a counter force on the stud retainer.

Figure 15:
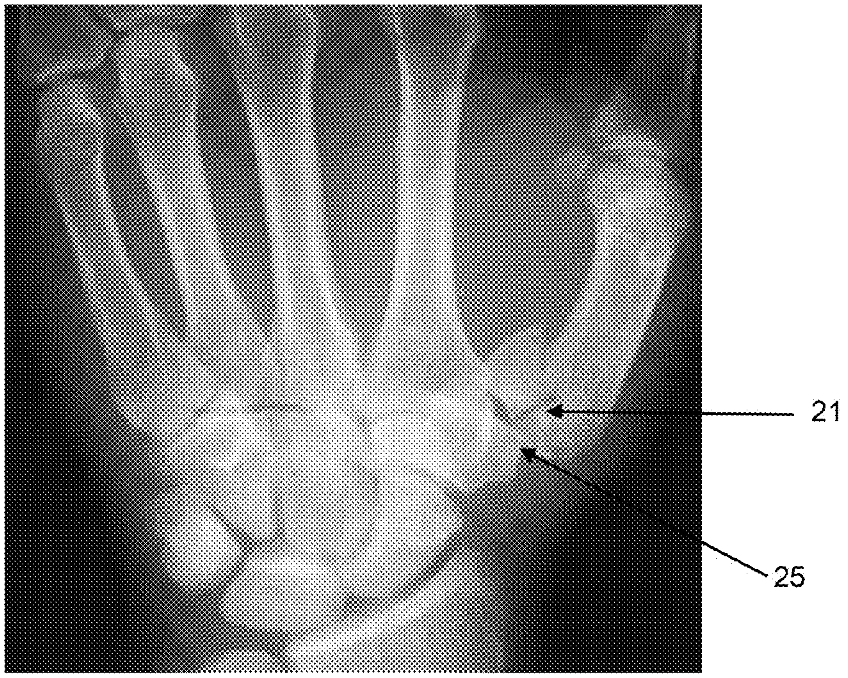
FIG. 15 shows an X-ray of a fractured thumb, wherein the fracture is proximal to a joint or bone gap.

FIG. 15 shows an X-ray of a fractured thumb, wherein the bone fracture 21 is proximal to a joint or bone gap 25.

Figure 16:
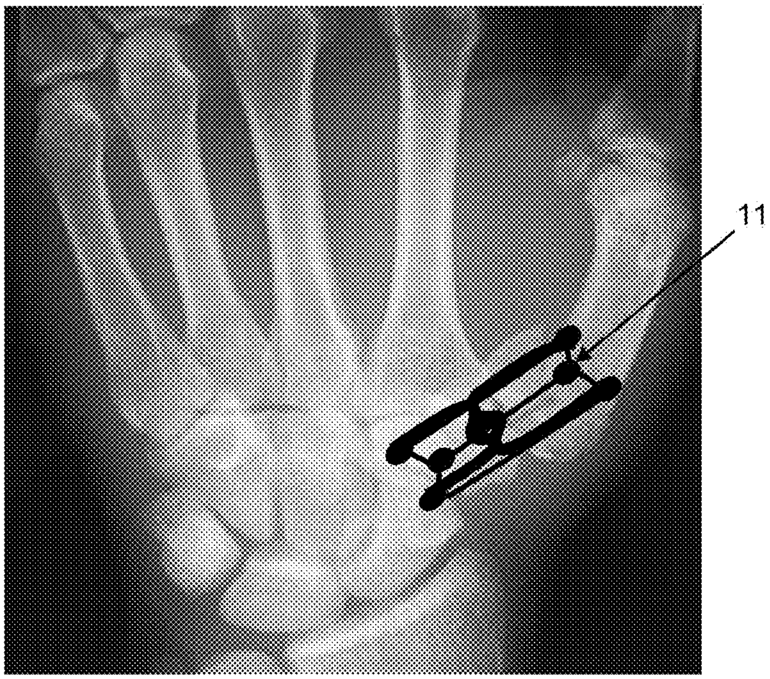
FIG. 16 shows the X-ray of FIG. 15 with an exemplary tensegrity external fixator coupled over the joint.

FIG. 16 shows the X-ray of FIG. 14 with an exemplary tensegrity external fixator 11 coupled over the joint.

Figure 17:
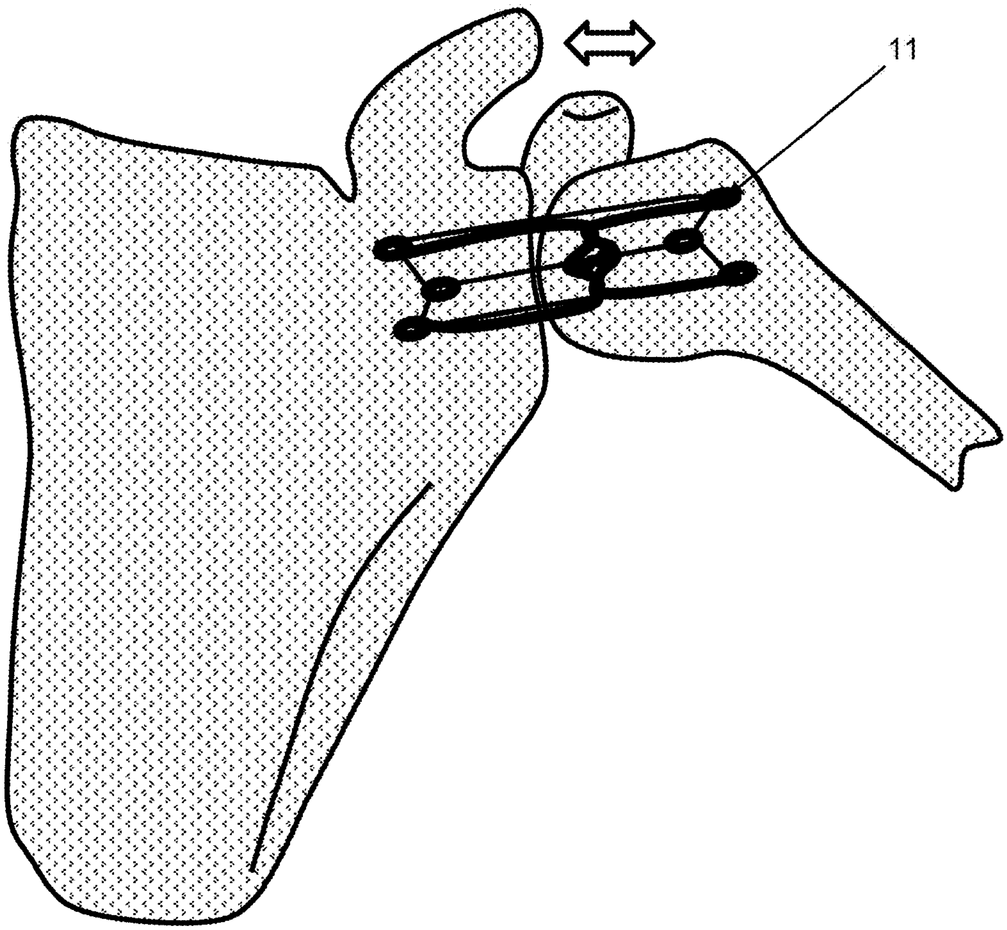
FIG. 17 shows a shoulder joint with an exemplary tensegrity external fixator coupled to the bones on either side of the shoulder joint.

FIG. 17 shows a shoulder joint with an exemplary tensegrity external fixator 11 coupled to the bones on either side of the shoulder joint.

Figure 18:
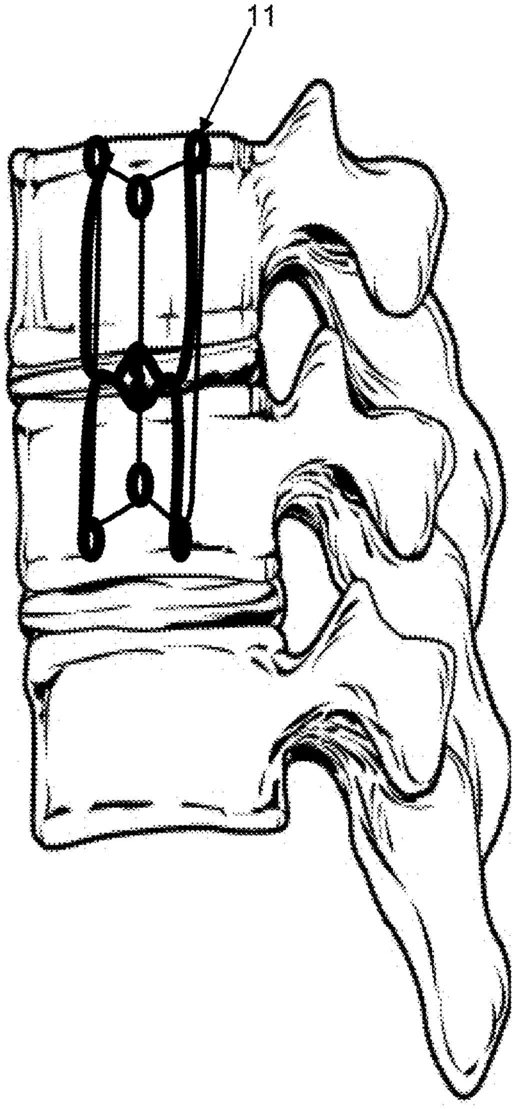
FIG. 18 shows a side view of vertebrae with an exemplary tensegrity external fixator coupled to the bones of adjacent vertebrae.

FIG. 18 shows a side view of vertebrae with an exemplary tensegrity external fixator 11 coupled to the bones of adjacent vertebrae. In this application of the exemplary tensegrity external fixator 11 may be configured under the skin, or may be an implantable device, wherein the stud has no exposed end that extend outside of the body.

Figure 19:
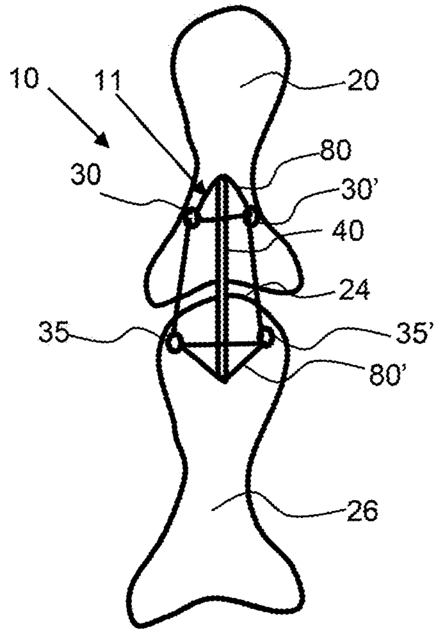
FIG. 19 shows a top view of an exemplary tensegrity external fixator coupled to the bones on either side of a joint wherein the exemplary tensegrity external fixator incorporates a single extension that is put in compression by the two separate tension bands on either end of the extension.
Figure 20:
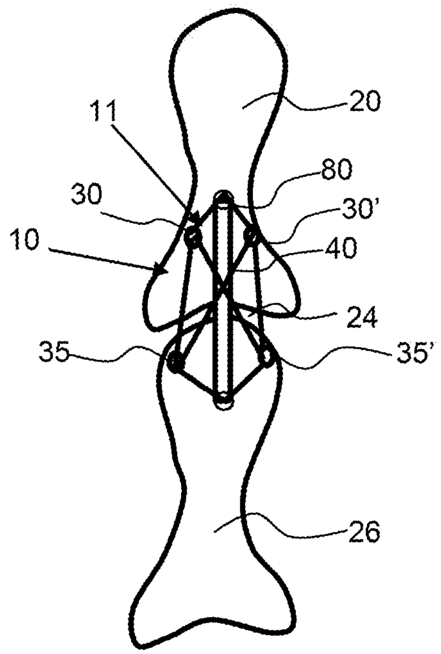
FIG. 20 shows a top view of an exemplary tensegrity external fixator coupled to the bones on either side of a joint wherein the tension band is coupled with two studs on either side of joint.
Figure 21:
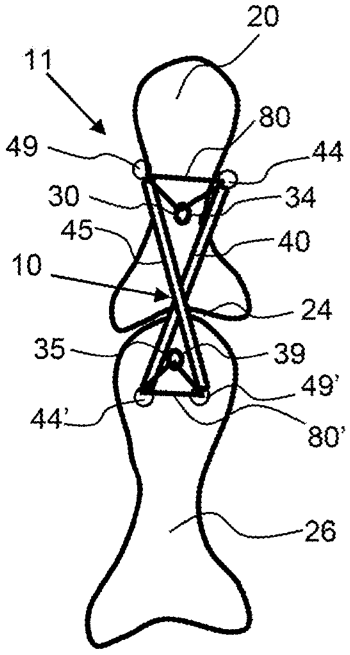
FIG. 21 shows a top view of an exemplary tensegrity external fixator coupled to the bones on either side of a joint wherein two crisscrossing extensions are put in compression by the two separate tension bands on either end of the extension.

Referring now to FIGS. 19 to 21, an exemplary tensegrity external fixator 11 is coupled to the first bone 20 and second bone 26 and on either side of a joint 24. The exemplary tensegrity external fixator produces tension on the joint to enable proper healing of the bone fracture and retain range of motion over the joint.

As shown in FIG. 19, the exemplary tensegrity external fixator 11 incorporates a single extension 40 that is put in compression by the two separate tension bands 80, 80' on either end of the extension. The extension may bow under the compression like an archery bow prior to launching an arrow. In this example, two studs 30, 30' are configured in the first bone 20 and two studs 35, 35' are configured in the second bone 26.

As shown in FIG. 20, an exemplary tensegrity external fixator 11 incorporates a single extension 40 that is put in compression. The tensegrity external fixator is coupled to the bones, first bone 20 and second bone 26, on either side of a joint 24 wherein a single tension band 80 is coupled with two studs on either side of joint. In this example, the single tension band crisscrosses the single extension 40 to compress the extension while pulling on the tension retainers coupled with the studs 30, 30' and 35, 35'.

As shown in FIG. 21, two extension 40, 45, crisscross between the two studs 30, 35. The two crisscrossing extensions are put in compression by the two separate tension bands 80, 80' on either end of the extensions. Each of the tension bands form a loop that extends between the tension retainers extending distal the stud retainer on either end of the compression assembly. On the first end, the tension band 80 extends through tension retainers 49 and 44 and through stud retainer 34 to form a loop, and on the second end, tension bad 80' extends through tension retainers 49' and 44' to form a complete loop.

Figure 23:
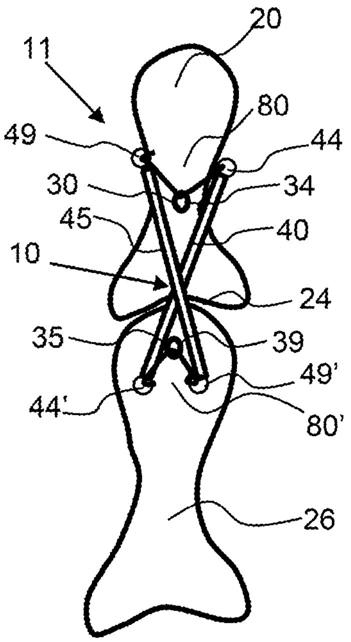
FIG. 23 shows a top view of an exemplary tensegrity external fixator coupled to the bones on either side of a joint wherein two crisscrossing extensions are put in compression by the two separate tension bands on either end of the extension.

As shown in FIG. 23, a similar arrangement is shown as that of FIG. 21, except that the tension bands 80 and 80' are not full loops, they extend are linear bands coupled to the tension retainers and retained by the stud retainers, such as being positioned in a detent.

Figure 22:
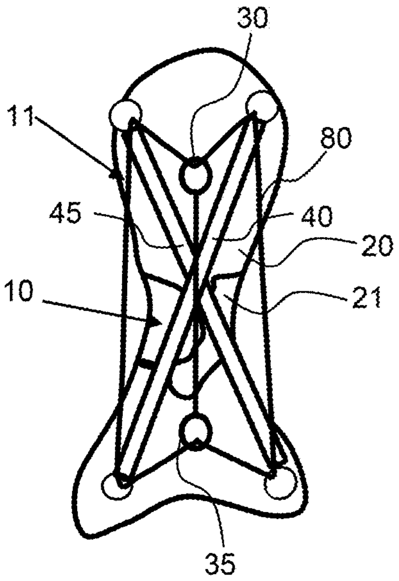
FIG. 22 shows a top view of an exemplary tensegrity external fixator coupled to a bone on either side of a fracture in said bone.

As shown in FIG. 22, an exemplary tensegrity external fixator 11 is coupled to a bone on either side of a bone fracture 21 in said bone 20. The first stud 30 is configured in a first bone portion 22 and the second stud 35 is configured in a second bone portion 29, opposite the first bone portion with respect to the bone fracture. This is to show that the tensegrity external fixator may be used for distracting a single bone and not necessarily over a joint.

Figure 24:
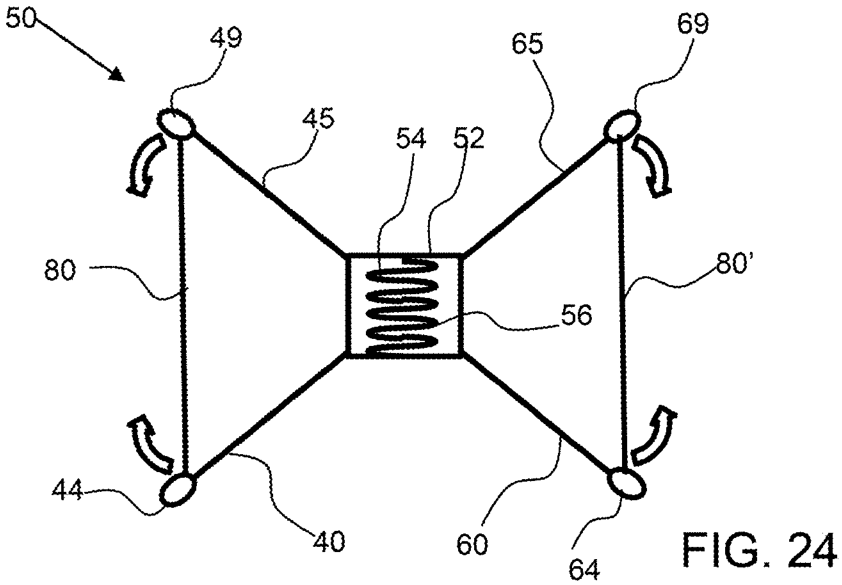
FIG. 24 shows a top view of an exemplary compressor assembly with pairs of extensions extended outward from opposing sides of the compressor coupler and ready to be compressed inward toward each other.
Figure 25:
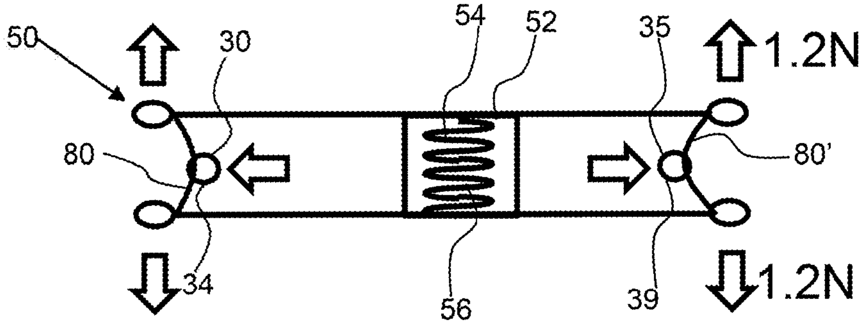
FIG. 25 shows a top view of the exemplary compressor assembly shown in FIG. 3, with the pair of extensions on either side of the compressor coupling forced inward toward each other and a tension band on either side to retain the pair of extensions effectively parallel with each other.
Figure 26:
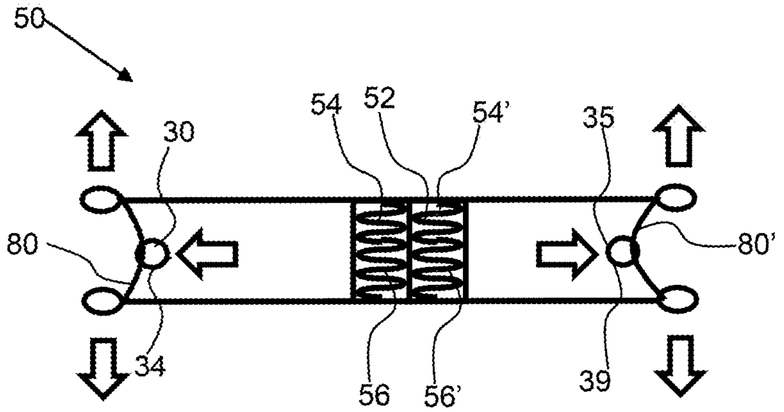
FIG. 26 shows a top view of the exemplary compressor assembly having a separate compression element for each pair of extensions.

As shown in FIGS. 24 to 26, an exemplary compression assembly 50 comprises a first extension 40 and second extension 45 on a first side of the compressor coupling 52 and a third extension 60 and fourth extension 65 on a second and opposing side of the compressor coupling. A compressor coupling may include a compression element 54, such as a spring 56, that is compressed when the extension on either side are forced towards each other. In an exemplary embodiment, a compression assembly may have a preset compression force wherein an approximate force will be required to force the extensions on either side of the compressor coupling into parallel alignment with each other, as shown in FIG. 25, wherein the force on each of the second and third extension arms is 1.2 Newtons. This preset compressor assembly may enable a surgeon to select a desired force from a range of compressor assemblies. As shown in FIG. 26, a compressor coupling 52 may comprise separate compression elements, 54, 54' for the opposing sets of extensions. Separate compression elements may provide for more precise control of the forces upon deflection of the arms inward. As shown in FIG. 26, two separate tension bands 80, 80' are configured between the first and second extensions and the third and fourth extensions, respectively. This type of compression assembly may be very quick and easy to implement for the surgeons. The compression bands may be elongated until the extensions are forced together and the compression bands may then be coupled to the stud retainers, 34, 39.

Figure 27:
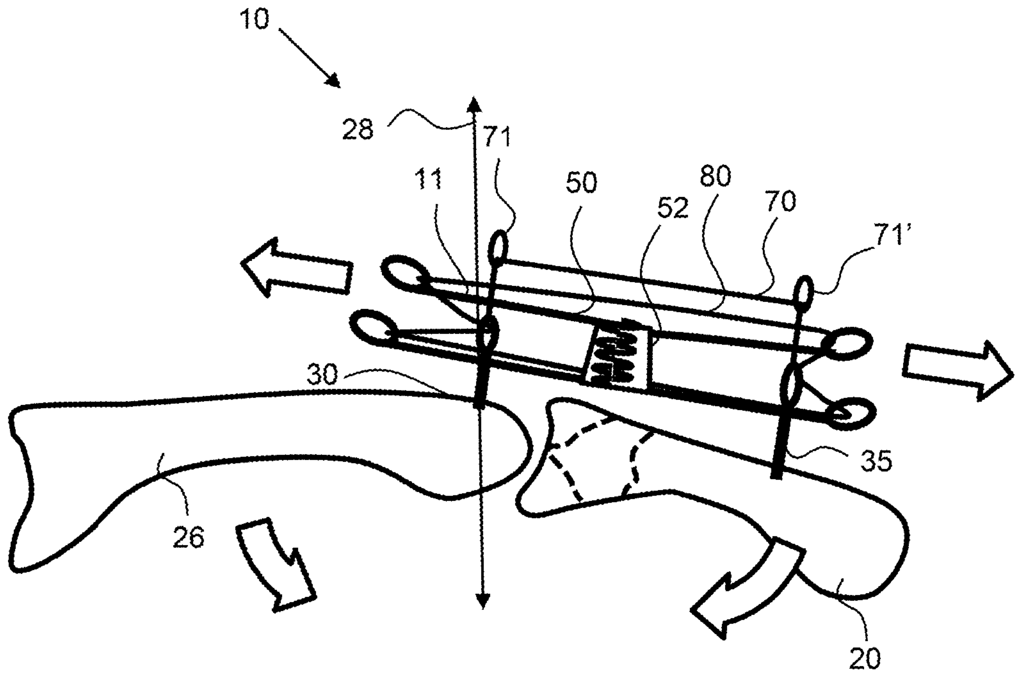
FIG. 27 shows a side view of an exemplary tensegrity external fixator with compressor assembly rotating with the bone of the finger about the joint.

As shown in FIG. 27, the compressor assembly 50 as shown in FIG. 24 is coupled to the first stud 30 and second stud 35 by the tension band 80, to distract the first bone 20 and second bone 26. Also, a torque stabilizer coupler 70 extends between and produces a tension force to pull the two torque stabilizers 71, 71' toward each other.

Figure 28:
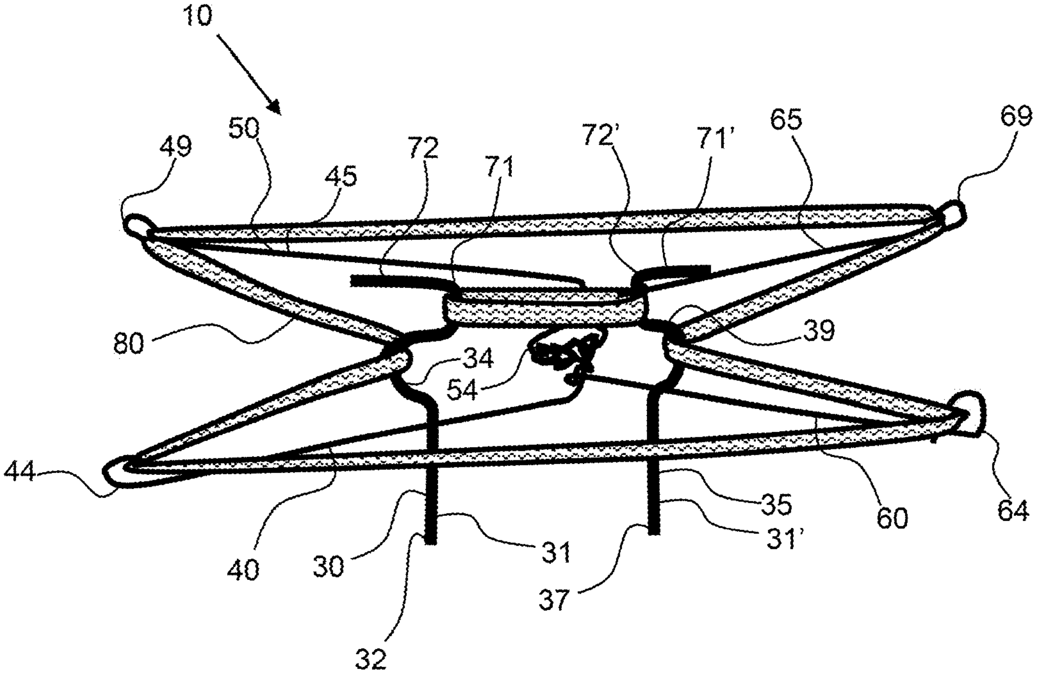
FIG. 28 shows an exemplary tensegrity external fixator system having a pair of torque stabilizers with a torque stabilizer coupler, an elastic band, pulling the torque stabilizers toward each other, to balance the torque force on the two studs proximal to the insert ends.

As shown in FIG. 28, an exemplary tensegrity external fixator system 10 has a pair of torque stabilizers 71, 71' with a torque stabilizer couple 70, an elastic band, pulling the torque stabilizers toward each other, to balance the torque force on the two studs proximal to the insert ends. Each of the first stud 30 and second stud 35 have a stud retainer 34, 39, and a torque stabilizer retainer 72, 72', respectively formed from a single shaped stud. The stabilizer coupler 70 may be an elastic band that can be changed out as required to properly balance the torque on the insert ends 32, 32' of the pair of studs. The compressor assembly 50 has first extension 40 with a first extension retainer 44, a second extension 45 with a second extension retainer 49, a third extension 60 with a third extension retainer 64 and a fourth extension 65 with a fourth extension retainer 69. A tension band 80, an elastic band extends through each of the extension retainers and through the stud retainers 34, 39 to pull the first stud and second stud away or apart from each other. This effectively distracts the bone over a joint to aid in healing while maintaining a range of motion.

Figure 29:
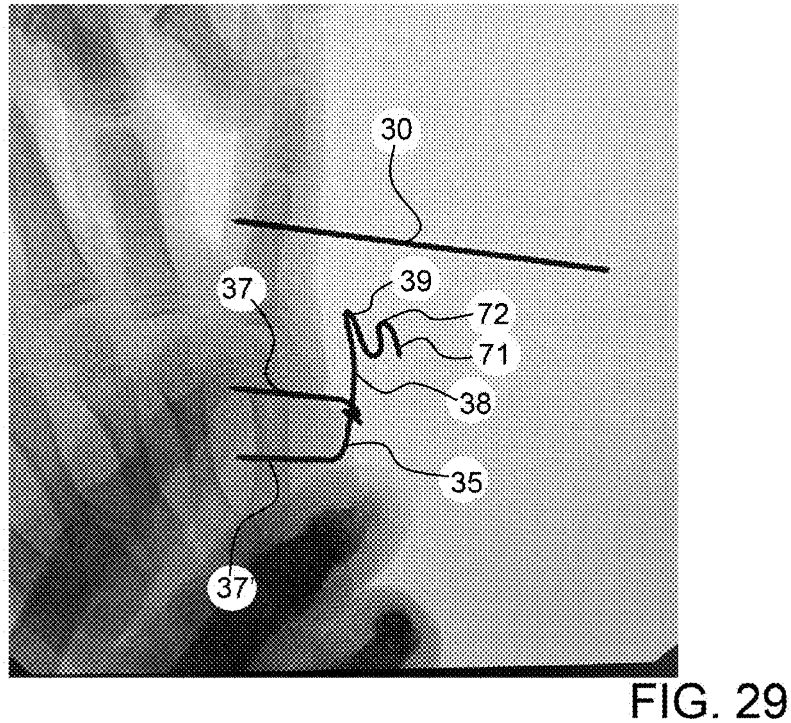
FIG. 29 shows an X-ray of a fractured hand with a first stud and a second stud having two insert ends into the bone with a stud extension extending to the stud retainer and a torque stabilizer.
Figure 30:
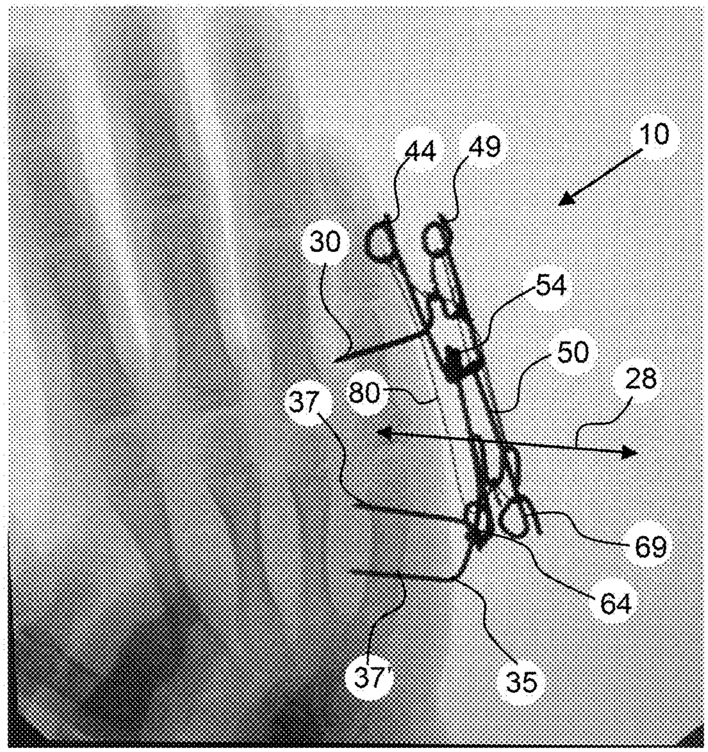
FIG. 30 show an X-ray of the fractured hand shown in FIG. 29, with a compressor assembly coupled to the first and second studs to distract the fractured bone.

Referring now to FIGS. 29 and 30, as shown in FIG. 29, a fractured hand has a first stud 30 and a second stud 35 having two insert ends 37, 37' inserted into a bone with a stud extension 38 extending to the stud retainer 38 and a torque stabilizer 71. The two insert ends of the second stud may more effectively prevent torque on the stud that may lead to displacement of the stud. The extension 38 enables the second stud retainer 39 to be located more proximal to the center of rotation 28. As shown in FIG. 30, a compressor assembly 50 is coupled to the first stud 30 and second stud 35 to distract the fractured bone. The compressor assembly 50 has first extension 40 with a first extension retainer 44, a second extension 45 with a second extension retainer 49, a third extension 60 with a third extension retainer 64 and a fourth extension 65 with a fourth extension retainer 69. A tension band 80, an elastic band extends through each of the extension retainers and through the stud retainers 34, 39 to pull the first stud and second stud away or apart from each other. This effectively distracts the bone over a joint to aid in healing while maintaining a range of motion. The exemplary tensegrity external fixator is positioned on the lateral aspect of the finger.

Figure 31:
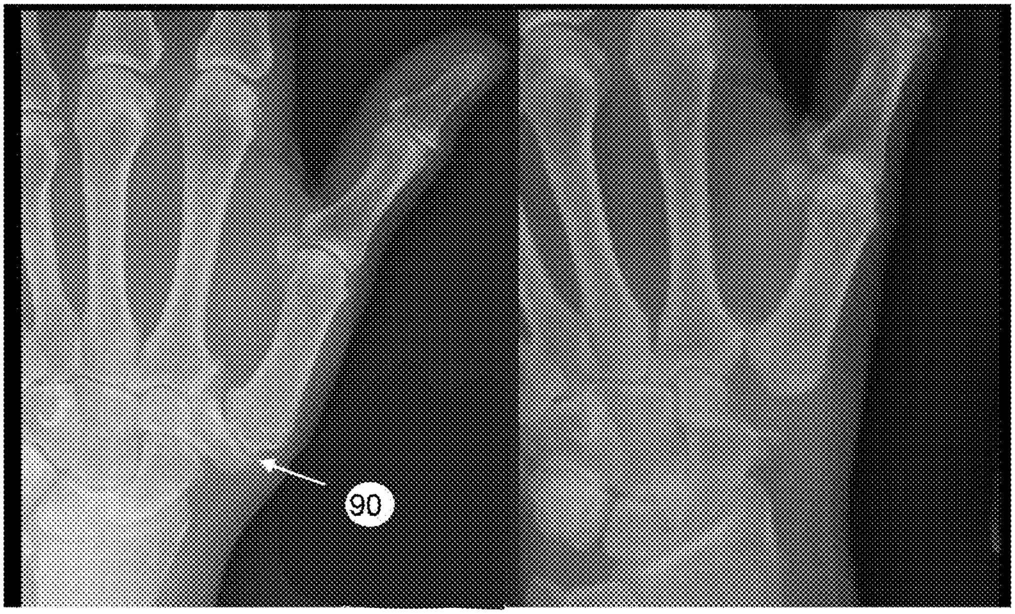
FIG. 31 shows a pair of X-rays of a hand with arthritis and with an arthroplasty site wherein the trapezium bone has been removed.
Figure 32:
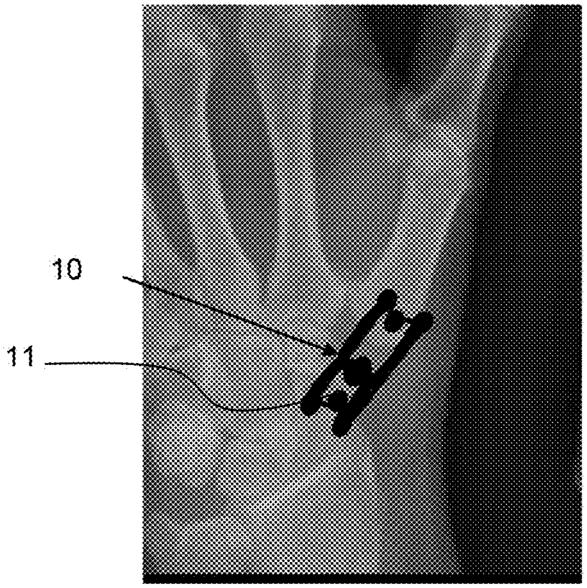
FIG. 32 shows an X-ray of the hand shown in FIG. 31 with an exemplary tensegrity external fixator coupled over the arthroplasty site.

Referring now to FIGS. 31 and 32, arthritis 90 is sometimes treated by arthroplasty, wherein in this example the trapezium bone has been removed. As shown in FIG. 32, an exemplary tensegrity external fixator 11 may be coupled over the arthroplasty site to draw together the metacarpal bone to the scaphoid bone.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A tensegrity external fixator system comprising a tensegrity external fixator comprising:

a) a first stud and a second stud, each comprising:
  i) an insert end;
  ii) a stud retainer;
 wherein in use, the first stud is attached to a first bone portion on a first side of a bone fracture and the second stud is attached to a second bone portion on a second side, opposing said first side, of said bone fracture;

b) a compressor assembly comprising:
  i) a first extension comprising:
   a first extended end having a tension retainer;
   a second extended end having a tension retainer; and
  wherein in use, the first extended end extends distal the first stud with respect to the bone fracture and the second extended end extends distal the second stud with respect to the bone fracture;

c) a tension band that extends between the tension retainer of the first extended end and the stud retainer of the first stud and applies tension to the stud retainer and first stud; and
  wherein the first stud and second stud are forced away from each other to place the first bone portion and second bone portion in traction;
  wherein the compression assembly comprises a compression element that is under compression when an extended end of the first extension is coupled with the tension band.

2. The tensegrity external fixator system of claim 1, wherein the first stud and second stud have an exposed end.

3. The tensegrity external fixator system of claim 1, further comprising a second tension band, wherein said second tension band extends between the tension retainer of the second extended end and the stud retainer of the second stud and applies tension to the stud retainer of the second stud.

4. The tensegrity external fixator system of claim 1, wherein the first stud and the second stud each further comprise a torque stabilizer, and wherein the tensegrity external fixator system further comprises a torque stabilizer coupler extending between and pulling the torque stabilizer of the first stud and the second stud toward each other.

5. The tensegrity external fixator system of claim 1, comprising two studs on said first side of the bone fracture, wherein the first tension band couples said two studs and the tension retainer of the first extended end of the first extension.

6. The tensegrity external fixator system of claim 5, comprising two studs on said second side of the bone fracture and a second tension band that couples said two studs on the second side of the bone fracture and the tension retainer of the second extended end of the first extension.

7. The tensegrity external fixator system of claim 5, comprising two studs on said second side of the bone fracture and wherein the tension band extends between said two studs on the second side of the bone fracture and the tension retainer of the second extended end of the first extension.

8. The tensegrity external fixator system of claim 1, comprising:
 a second extension comprising:
  a first extended end that extends distal the first stud with respect to the bone fracture and having a tension retainer;
  a second extended end that extends distal the second stud with respect to the bone fracture and having a tension retainer.

9. The tensegrity external fixator system of claim 8, wherein a single tension band couples the tension retainers of the second extension, the tension retainers of the first extension and the stud retainers of the first stud and second stud.

10. The tensegrity external fixator system of claim 8, comprising a second tension band;
 wherein the first tension band couples said first stud to the tension retainer of the first extended end of the first extension and the tension retainer of the first extended end of the second extension; and
 wherein said second tension band couples said second stud to the tension retainer of the second extended end of the first extension and the second extended end of the second extension.

11. The tensegrity external fixator system of claim 1, wherein the first bone portion and second bone portion are part of a single bone.

12. The tensegrity external fixator system of claim 1, wherein the first extension is a wire.

13. The tensegrity external fixator system of claim 1, wherein the tension band is an elastic band.

14. The tensegrity external fixator system of claim 1, further comprising a tensioning device that is coupled with the tension band to control an amount of tension exerted by the tension band.

15. The tensegrity external fixator system of claim 14, further comprising a tension controller coupled with the tensioning device and configured to change the tension of the tension band.

16. The tensegrity external fixator system of claim 15, wherein the tension controller automatically changes the tension of the tension band over time.

17. The tensegrity external fixator system of claim 15, wherein the tension controller is programmable to change the tension of the tension band over time.

18. The tensegrity external fixator system of claim 15, wherein the tension controller automatically varies the tension of the tension band in cycles.

19. The tensegrity external fixator system of claim 1, wherein the first bone portion is in a first bone and the second bone portion is a second bone.

20. The tensegrity external fixator system of claim 19, wherein the first stud is configured effectively at a center of rotation of the joint.

* * * * *